United States Patent
Hadvary et al.

(10) Patent No.: US 10,080,582 B2
(45) Date of Patent: Sep. 25, 2018

(54) MANUAL PRESSURE ACTIVATED APPLICATION MECHANISM

(71) Applicant: PharmaSens AG, Biel-Benken (CH)

(72) Inventors: Paul Hadvary, Biel-Benken (CH); Hansjorg Tschirky, Sissach (CH)

(73) Assignee: PharmaSens AG, Biel-Benken (CH)

( * ) Notice: Subject to any disclaimer, the term of this patent is extended or adjusted under 35 U.S.C. 154(b) by 122 days.

(21) Appl. No.: 14/391,410

(22) PCT Filed: Apr. 8, 2013

(86) PCT No.: PCT/EP2013/057324
§ 371 (c)(1),
(2) Date: Oct. 9, 2014

(87) PCT Pub. No.: WO2013/153039
PCT Pub. Date: Oct. 17, 2013

(65) Prior Publication Data
US 2015/0105691 A1    Apr. 16, 2015

(30) Foreign Application Priority Data

Apr. 11, 2012 (EP) .................................... 12163673

(51) Int. Cl.
*A61B 17/34* (2006.01)
*A61B 10/02* (2006.01)
(Continued)

(52) U.S. Cl.
CPC ...... *A61B 17/3403* (2013.01); *A61B 10/0266* (2013.01); *A61B 17/3415* (2013.01); *A61B 17/3496* (2013.01); *A61M 5/14248* (2013.01); *A61M 5/158* (2013.01); *A61B 2010/0208* (2013.01); *A61B 2017/3407* (2013.01); *A61B 2017/3409* (2013.01); *A61M 2005/14252* (2013.01); *A61M 2005/1585* (2013.01);
(Continued)

(58) Field of Classification Search
CPC .......................... A61M 5/158; A61B 17/3403
See application file for complete search history.

(56) References Cited

U.S. PATENT DOCUMENTS

| 6,685,675 B1 * | 2/2004 | Hadvary | ................. A61F 13/02 604/180 |
| 2002/0022798 A1 * | 2/2002 | Connelly | .......... A61M 5/14248 604/93.01 |

(Continued)

FOREIGN PATENT DOCUMENTS

| WO | WO 2008/078318 A2 | 7/2008 | |
| WO | WO 2011/119896 A1 | 9/2011 | |
| WO | WO 2011119896 A1 * | 9/2011 | ......... A61B 5/14503 |

*Primary Examiner* — Jeffrey G Hoekstra
*Assistant Examiner* — Nicholas E Kolderman
(74) *Attorney, Agent, or Firm* — Xsensus, LLP

(57) ABSTRACT

A skin insertion mechanism includes a needle fixedly positioned in a needle holder with a connector (or connective means) to an injection or analysis system having a skin attachment plate coated with an adhesive layer and a spacer mechanism kept in the ready-to-use position, the skin attachment plate is spaced away from a needle support covering the needle. Subcutaneous insertion of the needle is effected by attachment of the adhesive layer to the skin and releasing the spacer mechanism by applying a pre-set trigger point pressure against the skin.

14 Claims, 5 Drawing Sheets

(51) Int. Cl.
*A61M 5/158* (2006.01)
*A61M 5/142* (2006.01)
(52) U.S. Cl.
CPC ............... *A61M 2005/1586* (2013.01); *A61M 2005/1587* (2013.01)

(56) References Cited

U.S. PATENT DOCUMENTS

| | | | | |
|---|---|---|---|---|
| 2007/0191772 A1* | 8/2007 | Wojcik | .................. | A61M 5/158 604/158 |
| 2009/0093792 A1* | 4/2009 | Gross | ................ | A61M 5/14566 604/518 |
| 2009/0163874 A1* | 6/2009 | Krag | .................. | A61M 5/14248 604/180 |
| 2010/0137695 A1* | 6/2010 | Yodfat | .................. | A61B 5/6849 600/345 |
| 2011/0046456 A1* | 2/2011 | Hordum | ............ | A61M 5/14248 600/309 |

* cited by examiner

MANUAL PRESSURE ACTIVATED APPLICATION MECHANISM

FIELD OF THE INVENTION

The present invention is related with to an injection set or diagnostic probe attached to the skin and having subcutaneous access through a needle inserted into the skin. More specifically it is related to patch-type ports with a needle inserted into the skin and having connecting means to a pump or analysis system, or to syringe-type pens.

BACKGROUND OF THE INVENTION

Fields of application for this type of subcutaneous needle insertion mechanisms is the injection of physiologically active fluid into a patient, e.g. with insulin pump systems, or measurement of analyte levels in subcutaneous tissue. Further, it can be used in combination with syringes or pens. For these uses usually manual insertion of the needle into the skin is requested. Manual needle insertion creates often psychological aversion by the patient and bears safety hazards. Needle insertion mechanisms of prior art are normally complicated devices with multi-step handling requirements and are therefore not suited for simple patch-type ports with a needle inserted into the skin or for syringes or pens. In addition, such spring-type insertion mechanisms are unavoidably too abrupt and are therefore often perceived by the patient as disturbing.

The aim of the present invention is to provide a cost-effective and user-friendly solution allowing safe and easy insertion of a needle into the skin suitable for patch-type port systems and syringes or pens. According to the invention this is achieved as described in claim 1.

SUMMARY OF THE INVENTION

When used herein, the following definitions define the stated term.

Adhesive layer is composed of three parts, glue for fixing to the skin attachment plate, a textile providing the necessary flexibility and a glue for fixing onto the patient's skin. Suitable materials for temporary wearing on the skin with strong adhesive properties and minimal allergenicity are commercially available. This adhesive layer is fixed on the skin attachment plate preferentially using a surface which is significantly smaller than the surface attaching to the skin. This can be accomplished e.g. by an adhesive layer extending beyond the surface of the skin attachment plate or if a shape for the adhesive layer similar to or only slightly larger than the surface of the skin attachment plate is chosen, by fixing the adhesive layer to the skin attachment plate in such a way that an outer annular zone is not fixed to the skin attachment plate. Such a design is described in EP0825882 for a medical device with a rigid base.

Analyte means any endogenous or exogenous substance the concentration of which can be used to diagnose the health, organ function, metabolic status, or drug metabolizing capacity of an individual. Examples of endogenous substances are glucose, lactate, oxygen, creatinine, etc. Examples of exogenous substances are drugs, metabolites of such drugs, diagnostic substances (e.g. inulin) etc.

Analysis system comprises all elements necessary for determination of the concentration of analytes in subcutaneous tissue. Contacting of subcutaneous tissue is achieved via diagnostic probes with their active surface inserted into the skin.

Connector (or connective means) ensure a safe connection of the needle with an injection or analysis system. For connection to fluid delivery systems tight connections with minimal dead volume are important, such as cones e.g. Luer-Locks or septum-needle mechanisms. For microdialysis probes double-lumen connections are preferred. Connections of diagnostic probes, such as inserted sensors, to analysis systems, are mainly electrical or optical connections, known in the art.

Alternatively, the connector (or connective means) can in the ready-to-use position be separated from the needle holder with the fixedly positioned needle and only following skin insertion of the needle becoming connected to the needle. In a preferred embodiment the needle fixedly positioned in the needle holder protrudes from the needle holder not only towards the skin but also towards the connective means having a septum and pierces the septum upon movement of the needle holder towards the connector (or connective means).

Diagnostic probe is the functional element for the determination of analyte concentrations and means, but is not restricted to, any sensor, body fluid removal or microdialysis probe. The diagnostic probe is partially inserted into the skin and at least its active surface, located close to the inserted tip is in direct contact with the subcutaneous tissue. In the case that a diagnostic probe is inserted into the skin by means of a guide needle, this guide needle is retracted following insertion into the skin, preferentially together with the spacer mechanism and release element.

Functional package is designed to hold the skin insertion mechanism or device by a releasable coupling mechanism and has a peel-off cap to protect the sterility and to keep the active surface of diagnostic probes during storage in a defined environment, such as humidity. The functional package has also a rim element allowing, after removal of the cap, the correct attachment of the rim of the adhesive layer by pressing all-around against the skin. Further, the functional package protects the release element against premature, unintended operation and the release element can be actuated only following attachment of the skin insertion mechanism to the skin and removal of the functional package.

Injection systems for delivery of injection fluid encompass manually operated syringes and pumps being any combination of reservoir and delivery mechanism as known in the prior art, such as, but not limited to, syringe-type pumps, peristaltic pumps, piezoelectric pumps or consisting of a flexible reservoir squeezed by mechanical, pneumatic or hydraulic means. Delivery of injection fluid encompasses both relatively fast injection (bolus) and relatively slow introduction (also called injection or instillation) of a liquid into the body.

Means for attaching the outer rim of the adhesive layer firmly to the skin are construction elements securing attachment all-over upon pressing the skin insertion mechanism against the skin, thus ensuring safe and durable sticking of the skin attachment plate to the skin. Firm sticking of the entire flexible rim of the adhesive layer to the skin is of particular importance since small gaps not attached firmly are the potential nidus for easy detachment.

Examples for such means are a functional package with a rigid rim pressing the flexible rim of the adhesive layer protruding from the circumference of the skin attachment plate against the skin. Alternatively, the adhesive layer for attachment to the skin can have an equal circumference to the bottom of the skin attachment plate to which it is fixed only by a reduced surface in comparison to the adhesive surface attached to the skin, thus leaving a flexible rim which is important to avoid detachment from the skin. In such an embodiment the bottom of the skin attachment plate is pressing also the non-attached flexible rim of the adhesive layer firmly against the skin ensuring skin attachment all-over.

Means for coupling skin attachment plate with needle holder and decoupling from spacer mechanism and release element are constructed in such a way that these functions are automatically performed upon stacking-up of needle holder and skin attachment plate. Preferentially only axial pressure on the release element against the skin is needed for actuation of both functions. The needle holder and skin attachment plate get linked together forming with the inserted needle the subcutaneous port. Following decoupling the spacer mechanism from the needle holder, the release element together with spacer mechanism can be removed by simply lifting it off.

Microdialysis probes have a dialysis membrane as active surface forming the interface between the subcutaneous fluid and a dialysis fluid which is passed at the inner side of the membrane. In a preferred embodiment a micro-dialysis probe consists of an inner and an outer tube which is covered at the implantable part close to the tip by a dialysis membrane and the connecting means allow simultaneous coupling of the inner tube to a pump which delivers the dialysis fluid and the outer tube, as outlet for the dialysate to an analyte determining system or a microdialysate collection system.

Needles are functional elements with a tip being configured and being rigid enough to allow easy piercing the patient's skin and penetration into the skin. Insertion into the skin can be achieved in a minimally invasive and painless way if the diameter of the needle is very small, preferentially below 0.3 mm. These needles include, but are not restricted to, hollow needles such as cannulas for introducing an injection fluid, tubes or solid needles as diagnostic probes or tubes as guide needles for introducing flexible diagnostic probes, or solid needles as mandrins for introducing flexible tubes.

If the needle has the function of a guide needle or a mandrin it can be removed, preferentially linked with the removal of the spacer mechanism and release element.

Needle holder enforces the fixed positioning of the needle and has constructional features allowing an axially guided movement of the skin attachment plate relative to the needle holder via the spacer mechanism.

Release element releases the withholding means from the blocked ready-to-use position if a pre-set trigger point pressure is applied which results in sufficient acceleration of the skin insertion mechanism against the skin attachment plate to ensure skin piercing and insertion of the needle. The construction and materials used for the release mechanism are tuned to request such a trigger point pressure for release actuation.

The construction of the release element and of the withholding means is complementary, e.g. if the withholding means are using hook-type components for blockage, the release element can have protruding pin-shaped components releasing blockage by the hook-type components. In this construction, the bending of the hook-type components for de-blocking can define the necessary trigger point pressure for release, but also alternative constructions with e.g., a spring can be used for this purpose.

Septum is a stopper made of natural or synthetic rubber-type material which can be pierced with a cannula or wire in a contamination-free and tight way.

Skin attachment plate has preferentially a circular or oval footprint, is coated with an adhesive surface for attachment to the skin and has a hole opposing the tip of the needle with sufficient diameter to allow an unhindered passage of the needle upon moving the needle holder towards the skin attachment plate. The skin attachment plate is linked to the needle holder by the withholding means. The withholding means of the spacer mechanism is also ensuring a smooth axial movement, from the ready-to-use position in which the skin attachment plate and the needle holder are spaced from each-other so that the skin attachment plate is covering the tip of the needle, to a second position in which the skin attachment plate and the needle holder are close to each-other, and the needle is protruding through the hole of the skin attachment plate, inserted into the skin.

Spacer mechanism is the connecting element between the needle holder and the skin attachment plate. In the ready-to-use position of the skin insertion mechanism it keeps by its withholding means needle holder and skin attachment plate in parallel planes sufficiently spaced from each-other, so that the skin attachment plate is covering the tip of the needle. The spacer mechanism allows a guided axial movement of the skin attachment plate against the needle holder upon release of its withholding means actuated by the release element.

Withholding means are part of the spacer mechanism and fixing the skin attachment plate spaced from the needle holder in the ready-to-use position. Actuated by the release element, they allow a rapid release from this position if a predefined pressure is applied on the release element, sufficient to accelerate the needle holder for penetration of the skin by the needle.

DESCRIPTION OF THE DRAWINGS

In the following preferred embodiments of the invention are described with reference to the accompanying drawings in which FIGS. 1 *a,b* show a diagrammatic sectional view of a skin insertion mechanism in the ready-to-use position according to one embodiment of the invention.

DESCRIPTION OF THE INVENTION

Figure 1A:
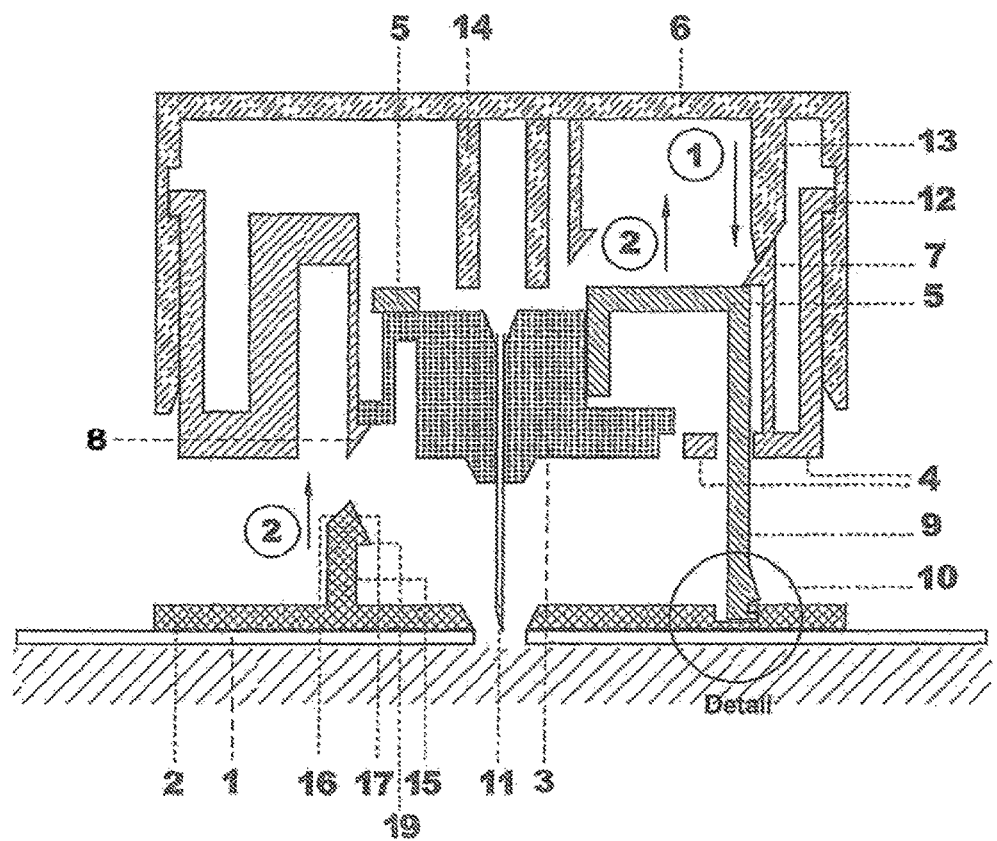
Figure 1B:
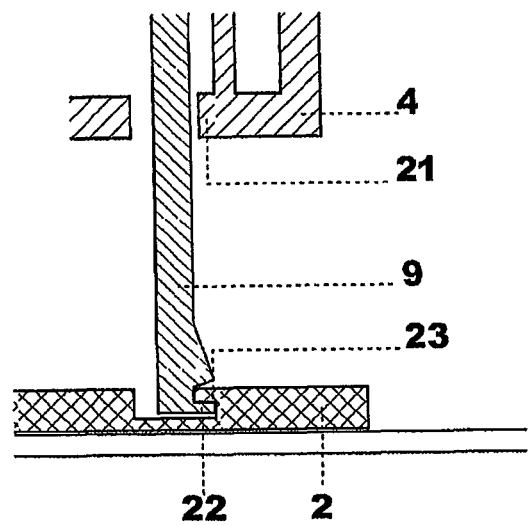

FIG. 1 shows the skin insertion mechanism in the ready-to-use position attached to the skin by the adhesive layer 1 of the skin attachment plate 2. The needle holder 3, the spacer mechanism consisting of the coupling element 4 and the withholding means 5, and the release element 6 have in this embodiment a 3-fold rotation axis; therefore, in the cross section shown the right part and the left part are depicting different cuts through the constructive elements.

The coupling element 4 of the spacer mechanism is linked to the withholding means 5 by the hook-type mechanism 7 and engages with the needle holder by the hook-type mechanism 8. The withholding means 5 has preferentially pin-shaped elements 9 and is holding the skin attachment plate by an engagement mechanism 10 in a distance from the needle holder 3 sufficient to ensure that it covers the cannula 11 and protects it from contacting the skin. The spacer mechanism 4 is linked to the release element 6 by a ridge and groove construction 12 allowing a limited relative movement of the release element in the direction towards the skin attachment plate (indicated by the arrow (1)).

Upon pressing the release element 6 towards the skin attachment plate, the pin-shaped protrusions 13 effect a bending of the hook-type mechanism 7 and decoupling from engagement with the withholding means 5. This decoupling mechanism requires a pre-defined pressure for actuation which is preferentially preset by the necessary pressure to bend the hook-type mechanism 7 or alternatively, by a separate pressure spring between the spacer mechanism 4 and the release element 6 (not shown).

Following decoupling and under the applied manual pressure, the release element moves relative to the withholding means 5 together with the skin attachment plate 2 in the direction indicated by arrow (2), and the supports 14 enforce the movement of the needle holder 3 together with the release element.

The construction of the hook-type mechanism 7 together with the pin-shaped protrusions 13 is dimensioned such that a pre-set trigger point pressure against the skin attachment plate is required for decoupling and releasing the withholding means, thus resulting in an axial movement of the needle holder towards the skin attachment plate with sufficient velocity for piercing the skin and insertion of the needle into the skin. The pin-shaped protrusion 15 of the skin attachment plate 2 is formed such, that it can effect two functions consecutively once the skin attachment plate approaches the needle holder: first, the hook-type mechanism 8 is bent by the wedge-shaped end 16 and decouples the spacer mechanism 4 from the needle holder 3. Second, the other wedge-shaped end 17 is bending the stays 18 of the needle holder, allowing the passage of the wedge-shaped end 18, and upon returning of the stays 18 into the initial position an engagement results between the skin attachment plate and the needle holder by the hook 19, as shown in FIG. 2.

Figure 2:
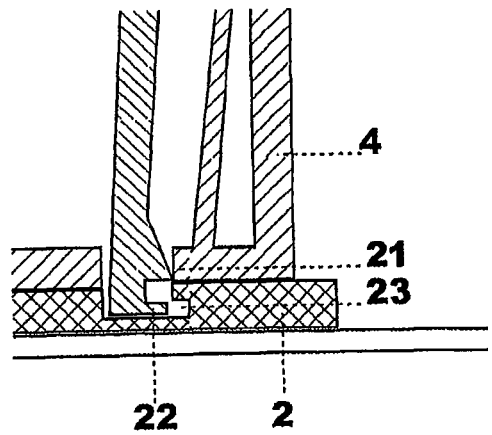
FIGS. 2 *a,b* show a diagrammatic sectional view of a skin insertion mechanism following needle insertion into the skin.
Figure 2A:
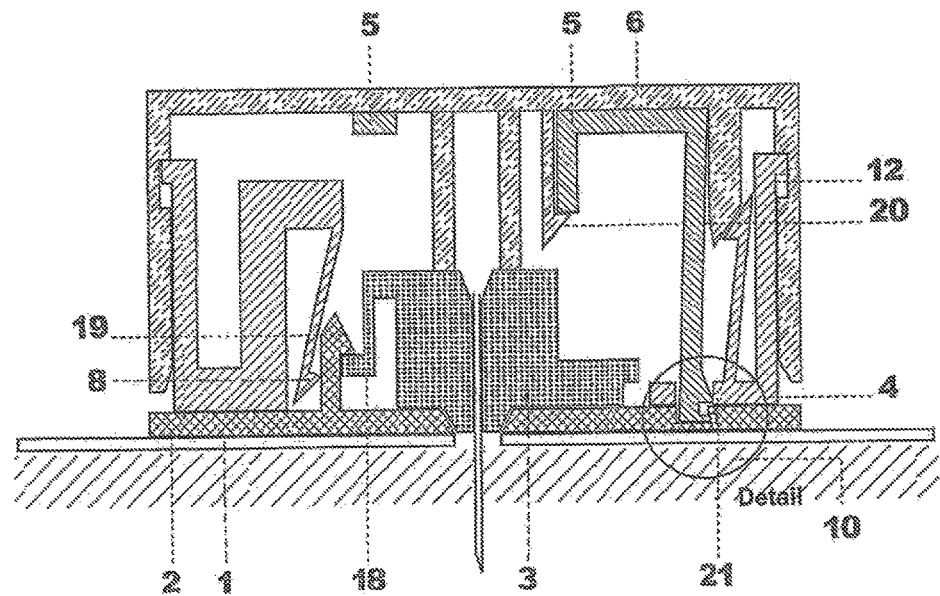

FIG. 2 depicts the situation following pushing the release element 6 towards the skin attachment plate, and as a result, needle insertion into the skin. The skin attachment plate 2 and the needle holder 3 are stacked up and held together by the hook 19 engaged with the stays 18 of the needle holder. Also the withholding means 5 and the release element are now stacked up and held together by the hook mechanism 20. The engagement mechanism 10 of the pin-shaped elements 9 with the skin attachment plate 2 has been decoupled by the edge 21 of the coupling element 4 and the spacer mechanism together with the release element can be removed.

Figure 3:
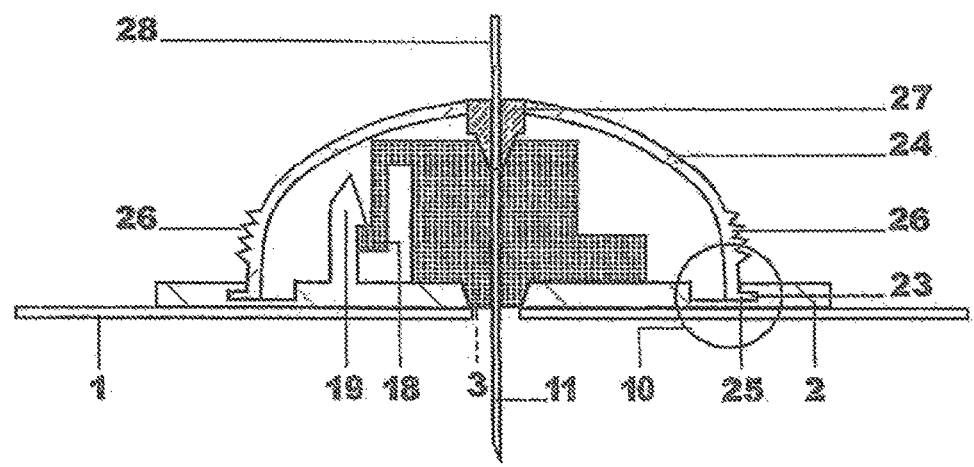
FIG. 3 is a diagrammatic sectional view of a skin insertion mechanism in the operational mode.

In this position, lifting off the release element engaged with the spacer mechanism through the ridge and groove construction 12 holding the coupling element 4 and with the withholding means 5 by the hook mechanism 19 results in removal of the spacer mechanism and the release element together, leaving only the needle holder attached to the skin by the skin attachment plate's adhesive layer, as shown in FIG. 3.

Details 1A and 2A show the engagement mechanism 10 for the engaged position of FIG. 1 and the decoupled position of FIG. 2, respectively. In Detail 1A the key 22 of the pin-shaped elements 9 of the withholding means is engaged with a slot 23 of the skin attachment plate 2, whereas in Detail 2A the pin-shaped elements 9 are bent by the edge 21 of the coupling element 4 resulting in decoupling of the skin attachment plate 2.

FIG. 3 shows the skin insertion mechanism in the operational mode. The skin attachment plate 2 is attached to the skin by the adhesive layer 1 and the needle holder 3 with the needle 11 inserted into the skin is fixed to the skin attachment plate by the stays 18 of the needle holder and the hook 19 of the skin attachment plate. The cover 24 is fixed to the skin attachment plate by the protrusion 25 engaging into the slot 23 of the engagement mechanism 10. This can be achieved e.g. by pressing the opposite sides of the cover against each other using the grip-shaped surface 26. The cover holds connector (or connective means) 27 with a tube 28 which can be connected to an injection system (not shown). The cover is formed such that it exerts a pressure on the connector (or connective means) for tight connection. The connective means can be e.g. cones such as Luer-Locks (depicted in the figure) or a septum-needle mechanism (not shown).

Figure 4:
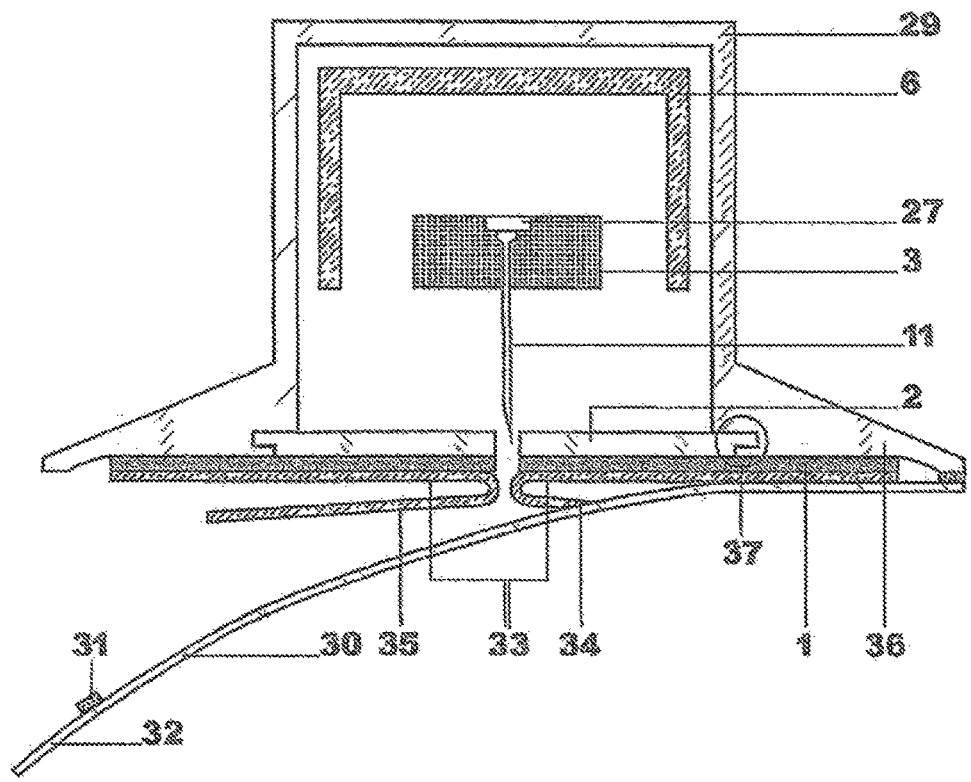
FIG. 4 is a diagrammatic sectional view of a skin insertion mechanism within a functional package.

FIG. 4 shows the diagrammatic cross section of a skin insertion mechanism within a functional package. The skin insertion mechanism is essentially similar to the one depicted in FIG. 1; therefore the spacer mechanism is not shown and only the skin attachment plate 2 coated with the adhesive layer 1, the release element 6, the needle holder 3 with the needle 11 and a septum as the connector (or connective means) are depicted schematically.

The functional package 29 protects the release element 6 against unintended activation. The peel-off foil 30 with the seal 31 closes the package hermetically and keeps it sterile during storage. Pulling the flap 32 for stripping the peel-off foil pulls off also one part of the adhesive layer protection 33, which is fastened to the peel-off foil by the glue 34. In addition, a tongue 35 of the other part of the adhesive layer protection 33 gets easily accessible for liberating the rest of the adhesive layer without hazard of sticking-together problems of the liberated flexible rim.

The functional package 29 can now be pressed against the skin and its rim 36 secures firm attachment of the adhesive layer 1 all-over which is important for ensuring safe and durable sticking of the skin attachment plate to the skin. A slight axial turn of the functional package disconnects the bayonet joint 37 and it can be lifted-off from the skin insertion mechanism attached to the skin in the ready-to-use position, as described in FIG. 1.

Figure 5:
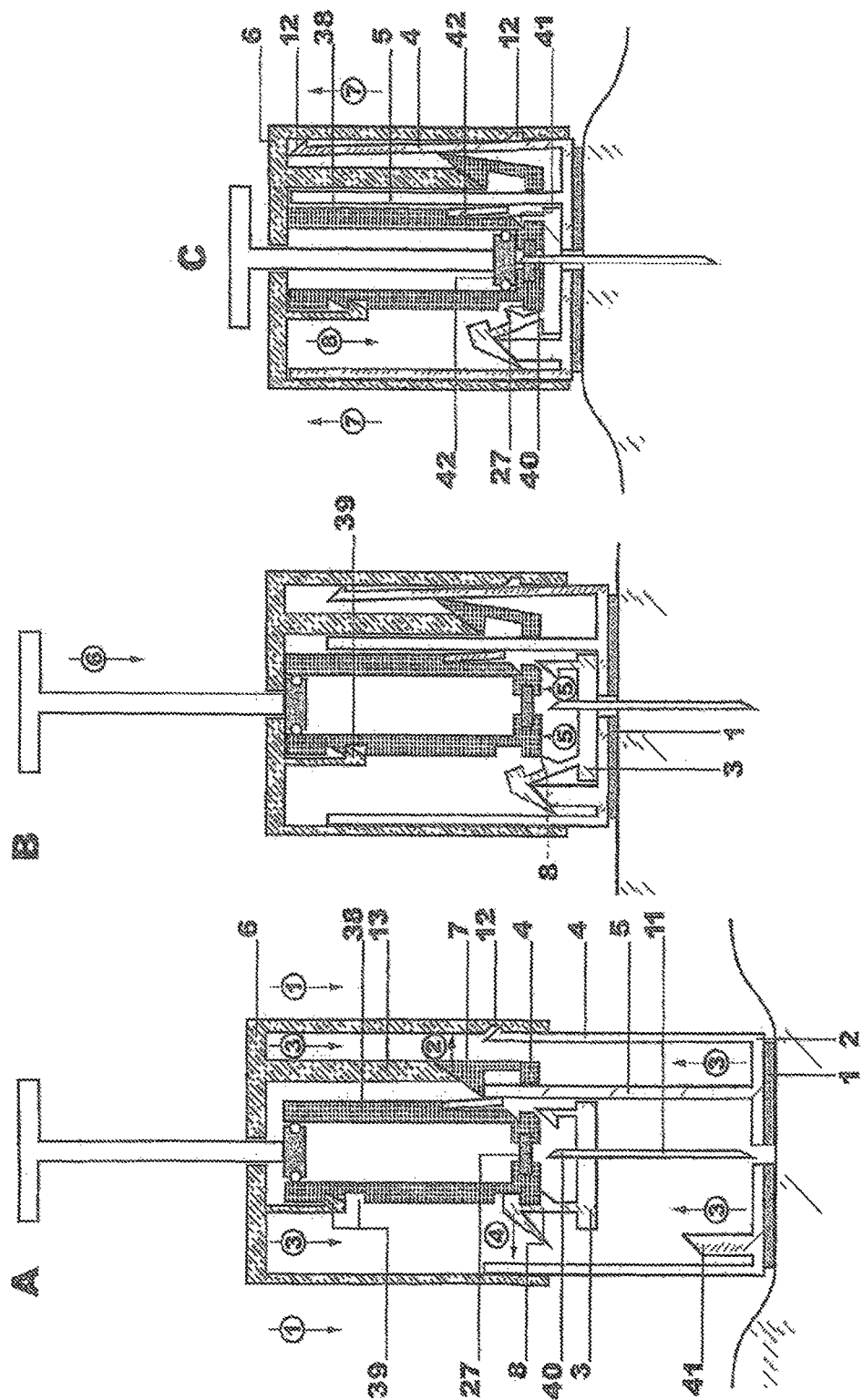
FIG. 5 is a diagrammatic sectional view of a skin insertion mechanism with an integrated syringe for injection of fluid.

FIG. 5 shows the diagrammatic cross section of a skin insertion mechanism with an integrated syringe or pen for injection of fluid. Such an embodiment of the subject invention has several advantages compared to solutions in prior art for the different functionalities needed for safe and easy self-application of injection fluid with single-use syringes or pens.

In particular, attachment to the skin by an adhesive layer avoids the danger that the skin is dented by the needle resulting in incomplete or even no insertion or unintended retraction from the skin during manipulation before concluding injection. Further, entirely manual insertion of the needle without mechanistic support results in psychological aversion and mostly not enough speed to safely piercing the skin. On the other hand, insertion of the needle attached to the syringe or pen by a spring-type mechanism is unavoidably too fast resulting in shocking the patient and sometimes in the reflex of retraction. In contrast, by the constructional pre-set trigger point pressure against the skin attachment plate for releasing insertion of the needle, making use of the natural arm movement characteristics, a smooth but sufficiently fast movement of the needle against the skin can be achieved for safe piercing the skin by the needle tip and inserting the needle into the skin.

The example shown in FIG. 5 guides and facilitates all necessary manipulations for safe use. The minimal handling requirements by the patient, needing only axial pressure against the skin and pulling from the skin upon conclusion of injection are easily performed also by elderly patients with reduced manual skills. The different stages of handling and functions are depicted in the FIGS. 5A to 5C.

FIG. 5A shows an embodiment of the skin insertion mechanism with an integrated syringe in the ready-to-use position, attached to the skin by the adhesive layer 1 of the skin attachment plate 2. The needle holder 3, the spacer mechanism consisting of the coupling element 4 and the withholding means 5, and the release element 6 have in this embodiment a 3-fold rotation axis; therefore, in the cross section shown the right part and the left part are depicting different cuts through the constructive elements.

The coupling element 4 of the spacer mechanism is linked to the withholding means 5 by the hook-type mechanism 7 which is part of the syringe housing 38, which in turn engages with the needle holder by the hook-type mechanism 8. The withholding means 5 consists in this embodiment of pin-shaped elements fused with the skin attachment plate 2 and keeps the skin attachment plate in a distance from the needle holder 3 sufficient to ensure that it covers the cannula 11 and protects it from contacting the skin. The spacer mechanism 4 is in this embodiment also fused with the skin attachment plate and is linked to the release element 6 by a hook and groove construction 12 allowing the movement of the release element in the direction towards the skin attachment plate (indicated by the arrow (1)).

Upon pressing the release element 6 towards the skin attachment plate, the pin-shaped protrusions 13 effect a bending of the hook-type mechanism 7 in the direction of the arrow (2) and decoupling from engagement with the withholding means 5. This decoupling mechanism requires a pre-defined pressure for actuation which is preferentially preset by the necessary pressure to bend the hook-type mechanism 7.

Following decoupling and under the applied manual pressure, the release element moves relative to the withholding means 5 and the skin attachment plate 2 axially, as indicated by arrows (3), and as soon as the release element touches the syringe housing 38 they are linked together by the hook mechanism 39 (as shown in FIG. 5B) and are moving together towards the skin attachment plate 2.

In this embodiment the connector (or connective means) 27 is a septum at the outlet of the syringe and the needle fixedly positioned in the needle holder has a part 40 projecting towards the connector (or connective means) and having a tip configured and dimensioned for piercing the septum and forming the outlet of the syringe once it has pierced through the septum. The connector (or connective means) 27 and the needle holder 3 are separated by the hook-type mechanism 8 until the pin-shaped protrusions 41 of the skin attachment plate 2 disconnect the hook-type mechanism 8 from the needle holder 3.

FIG. 5B shows an intermediate position of the skin insertion mechanism at the moment when the needle holder 3 has reached the skin attachment plate 2. Movement of the skin attachment plate 3 towards the needle holder 3 resulted first in the insertion of the cannula with the tip projecting toward the patient's skin into the skin. Consecutively, by decoupling the hook-type mechanism 8 which was fixing the needle holder 3 separated from the connector (or connective means) 27, the needle holder 3 can move towards the connector (or connective means) 27, pushed by the skin attachment plate 2.

FIG. 5C shows the end position of the skin insertion mechanism following delivery of the injection fluid into the skin of the patient, at the start of axial removal from the skin. The protruding part of the cannula 40 with its tip projecting toward the connector (or connective means) has pierced through the septum 27 forming the outlet of the syringe. The hook 41 has engaged with the syringe housing 38 and the injection fluid contained in the syringe has been emptied by pushing manually the piston towards the skin.

Removal of the entire device by pulling axially in the direction of the arrow (7) from the skin follows the following course (not shown in the figure): All parts are now fixedly held together and only the skin attachment plate 2, withhold by the adhesive layer 1 attached to the skin, can slide out of the release element 6 with the coupling element 4 and the withholding means 5 in the direction of the arrow (8), thus forming a protection shield of the needle 11 which has been pulled out of the skin. In the end position, defined by the hook and groove construction 12 the springy rib 42 blocks the possibility of sliding back of this protection shield of the needle. Further pulling and/or bending from the axial direction detaches the adhesive layer from the skin.

Upon reading these specifications, various alternative embodiments will become obvious to the skilled artisan. For example, the different mechanisms for connection and disconnection of the elements can be any construction known in prior art for this function like e.g. hooks, bayonet catches, elements deforming by pressing together and thereby spreading out besides and disconnecting from protrusions, magnetic elements, etc. and some of the movements can be re-enforced with suitable springy mechanisms.

The description in the drawings is focusing on the application as injection set or a syringe or pen with a cannula inserted into the skin but similar constructional features can be used also for diagnostic probes such as e.g. sensors or microdialysis probes.

The major advantage of a skin insertion mechanism of a needle described above is that it is very simple and safe to operate by the patient and avoids the psychological hurdle and possible failures in manually inserting a needle into the skin. Further, in contrast to spring-operated needle insertion mechanisms being unavoidably too fast resulting in shocking the patient and sometimes in the reflex of retraction, the insertion mechanism of the subject invention is smooth but the movement of the needle against the skin is sufficiently fast for safe piercing the skin by the needle tip and inserting the needle into the skin.

In addition, the means for firmly attaching the outer rim of the adhesive layer all-over to the skin is important for ensuring safe and durable sticking of the skin attachment plate to the skin for long-term attachment. By the subject invention this can be done very effectively and without the need to manually circling and pressing the rim against the skin which is problematic with small rims and clumsy fingers and the already inserted needle being a psychological barrier for adequate pressing.

The invention claimed is:

1. A skin insertion mechanism of a needle fixedly positioned in a needle holder and the skin insertion mechanism having a connector to an injection or analysis system, comprising:
   a) a skin attachment plate coated with an adhesive layer for attachment to a patient's skin and having a hole allowing the passage of the needle;

b) a spacer mechanism connected to and guiding an axial movement of the needle holder and the skin attachment plate relative to each other, the spacer mechanism comprising
   a withholder structure releasably connected to the needle holder and the skin attachment plate and keeping the needle holder and the skin attachment plate in a ready-to-use position axially fixedly spaced away from each other to cover the needle, and the withholder structure axially moving in a direction relative to the needle holder when released, and
   a coupling element keeping the needle holder and the withholder structure in the axial position by releasable connecting elements requiring a pre-set trigger point pressure to be released, and the coupling element axially moving in a direction of the axial movement of the needle holder when released; and
c) a release element movably linked to the spacer mechanism and provided with pressure exerting elements producing pressure onto the connecting elements by axial movement towards the needle holder to release the withholder structure from the ready-to-use position, and allowing the axial movement of the needle holder towards the skin attachment plate with sufficient velocity to pierce the skin by the needle and inserting the needle into the skin.

2. The skin insertion mechanism according to claim 1, further comprising a structure to exert pressure onto an outer rim of the adhesive layer extending beyond the skin attachment plate.

3. The skin insertion mechanism according to claim 2, wherein the structure to exert pressure onto the outer rim of the adhesive layer is a functional package with a rim pressing the adhesive layer towards the skin and protecting the release element against unintended activation.

4. The skin insertion mechanism according to claim 2, wherein a structure to firmly attach the outer rim of the adhesive layer to the skin is the skin attachment plate to which the adhesive surface for attachment to the skin is fixed by a reduced surface in comparison to the adhesive surface attached to the skin.

5. The skin insertion mechanism according to claim 1, further comprising a structure to couple the skin attachment plate with the needle holder and decouple from the spacer mechanism and the release element, and performing these functions automatically upon stacking-up of the needle holder and the skin attachment plate and allowing removal of the spacer mechanism together with the release element.

6. The skin insertion mechanism according to claim 5, wherein the structure to couple the skin attachment plate with the needle holder and decouple from the spacer mechanism and the release element includes hook-type elements actuated by the axial movement of the needle holder towards the skin attachment plate.

7. The skin insertion mechanism according to claim 1, wherein the needle is a cannula for subcutaneous delivery of injection fluid.

8. The skin insertion mechanism according to claim 1, wherein the needle is a plastic tube with a removable inner mandrin for insertion into the skin, the mandrin being removed together with the spacer mechanism and the release element.

9. The skin insertion mechanism according to claim 1, wherein the needle holder with the fixedly positioned needle and the connector to the injection system are separated in the ready-to-use position and get functionally connected only following needle insertion into the skin by consecutive stacking-up, first of the skin attachment plate with the needle holder, followed by stacking-up of the needle holder with the connector.

10. The skin insertion mechanism according to claim 9, further comprising a structure to couple the needle holder, the connector to the injection system, and the release element together, and performing these functions automatically upon stacking-up of the skin attachment plate, the needle holder and the connector to the injection system with the release element and allowing removal from the skin by pulling away from the skin as a unit, with the skin attachment plate being pulled by the adhesive layer attached to the skin and becoming fixed in a pulled-out position as needle protection.

11. The skin insertion mechanism according to claim 1, wherein the needle is a diagnostic probe.

12. The skin insertion mechanism according to claim 1, wherein the needle is a removable guide needle for insertion of a flexible cannula or diagnostic probe into the skin, the guide needle being removed together with the spacer mechanism and release element.

13. A method for injection of a fluid into the skin or determining analyte concentrations in a subcutaneous tissue by the steps of:
   a) attaching the skin insertion mechanism according to claim 1 to the skin of a subject,
   b) pressing the skin insertion mechanism against the skin by pressing on the release element with the pre-set trigger-point pressure,
   c) removing the spacer mechanism together with the release element, and
   d) connecting the needle to the injection or analysis system.

14. A method for injection of a fluid into the skin by the steps of:
   a) attaching the skin insertion mechanism according to claim 1 to the skin of a subject,
   b) pressing the skin insertion mechanism against the skin by pressing on the release element with the preset trigger-point pressure,
   c) introducing the fluid into the skin with a syringe-type fluid delivery system, and
   d) removing the skin insertion mechanism by pulling away from the skin.

* * * * *